United States Patent [19]

Kuffner et al.

[11] 3,956,311

[45] May 11, 1976

[54] PROCESS FOR THE PREPARATION OF 3-ANILINO-PYRAZOLONES-(5)

[75] Inventors: Karl Kuffner; Ernst Meier, both of Munich; Hans Glockner, Pullach, all of Germany

[73] Assignee: AGFA-Gevaert, A.G., Leverkusen, Germany

[22] Filed: Aug. 8, 1973

[21] Appl. No.: 386,582

Related U.S. Application Data

[63] Continuation-in-part of Ser. No. 175,702, Aug. 27, 1971, abandoned.

[30] Foreign Application Priority Data

Aug. 29, 1970 Germany............................ 2042821

[52] U.S. Cl. ............................................. 260/310 A
[51] Int. Cl.$^2$ ....................................... C07D 231/08
[58] Field of Search ............................... 260/310 A

[56] References Cited
UNITED STATES PATENTS

| | | | |
|---|---|---|---|
| 2,376,380 | 11/1942 | Porter et al. ..................... | 260/310 A |
| 3,127,269 | 3/1964 | Greenhalgh et al. ............. | 260/310 A |
| 3,470,191 | 9/1969 | Eerdekens et al. ............... | 260/310 A |

FOREIGN PATENTS OR APPLICATIONS

| | | | |
|---|---|---|---|
| 1,129,333 | 10/1968 | United Kingdom............. | 260/310 A |
| 1,129,334 | 10/1968 | United Kingdom............. | 260/310 A |
| 1,134,329 | 11/1968 | United Kingdom............. | 260/310 A |
| 1,176,478 | 8/1964 | Germany ........................ | 260/310 A |

OTHER PUBLICATIONS

Elderfield, Heterocyclic Compounds, (Wiley, N.Y., 1957), Vol. 5, p. 151.
Conant, et al., Chem. of Org. Compounds, (MacMillan, N.Y., 1947), 4th Ed., p. 335.

*Primary Examiner*—Henry R. Jiles
*Attorney, Agent, or Firm*—Connolly and Hutz

[57] ABSTRACT

Preparation of 1-aryl-3-anilino-pyrazolones-(5) by reacting a hydrazine with an ester from the group of dialkoxyacrylic acid ester, trialkoxy propionic acid ester or iminoalkoxy propionic acid ester to produce a β-hydrazine-β-alkoxyacrylic acid ester and then condensing this intermediate product with an aniline to result in the desired anilinopyrazolone. These reactions are carried out in a methanolic solution in the presence of an acetic acid catalyst.

1 Claim, No Drawings

PROCESS FOR THE PREPARATION OF 3-ANILINO-PYRAZOLONES-(5)

This application is a continuation-in-part of copending U.S. application Ser. No. 175,702, filed Aug. 27, 1971 for "Process for the Preparation of 3-Anilino-Pyrazolones-(5)" by Karl Kuffner and others, now abandoned.

Background of the Invention

This invention relates to a process for preparing 3-anilinopyrazolone-(5) in a conversion reaction in methanolic solution with glacial acetic acid as catalyst.

The processes for the preparation of these 3-anilinopyrazolones, taught in the patent literature, are not generally applicable. Thus, for example, the method disclosed in the U.S. Pat. No. 2,343,703, according to which aminopyrazolones react with anilines with the separation of ammonia, is not suitable with respect to many aniline derivatives — see German published patent application No. 1,237,580. This method fails also when certain phenyl-hydrazines with negative substituents are used, e.g. 2,4,6-trichlorphenylhydrazine. The improvement of this method, as disclosed in the Russian Pat. No. 141,485 and in the Belgian Pat. No. 670,949 here also do not lead to the goal. Also the method disclosed in the German published patent application No. 1,176,478, according to which arylisocyanates are reacted with sodium acetoacetic ester, is only applicable in a limited manner. Aside from the difficulty of preparing many substituted arylisocyanates, all substituents are disturbing which react with sodium acetoacetic ester. The method disclosed in the German published patent application No. 1,237,580, according to which malonic ester monoanilides are converted to $\beta$-chloro-$\beta$-arylaminoacrylic ester by chlorination with $PCl_5$ and these compounds are reacted with arylhydrazines, is limited to substitution products which tolerate the treatment with $PCl_5$. Many substituted malonic ester monoanilides become resinous by the chlorination with $PCl_5$. The process according to the German published application No. 1,101,429 — Conversion of Amidrazones with Anilines — has the disadvantage that the preparation of amidrazones is limited to certain substituents. A broader application is afforded by the methods disclosed in the British Pat. No. 1,129,333, 1,129,334 and 1,134,329, according to which $\beta,\beta$-dialkoxy-acrylic acid ester or $\beta$-amino-$\beta$-alkoxyacrylic acid ester chlorhydrate are converted with the arylamine to the corresponding 3-alkoxy-3-arylamino-acrylic acid esters which in turn are condensed with hydrazines to pyrazolone. But here, too, the yield or the purity of the products is often unsatisfactory.

It has now been found that good yields of 3-anilino-pyrazolones-(5) substantially free of by-products are obtained if a hydrazine is reacted with a dialkoxy acrylic acid ester, trialkoxy-propionic acid ester or iminoalkoxy propionic acid ester to produce a $\beta$-hydrazino-$\beta$-alkoxyacrylic acid ester if the reaction takes place in a methanolic solution with the glacial acetic acid as catalysts. The $\beta$-hydrazino-$\beta$-alkoxyacrylic acid ester is then condensed with a substituted or unsubstituted aniline with glacial acetic acid catalyst to produce 3-anilino-pyrazolone.

It is an object of this invention to provide an improved method of preparing 1-aryl-3-anilino-5-pyrazolones.

It is a further object to provide a preparation in which anilines of a basic character are combined with hydrazines of an acid character to result in anilinopyrazolones.

Summary of the Invention

According to the invention, it was determined the 1-aryl-3-anilinopyrazolones-(5) of the general formula

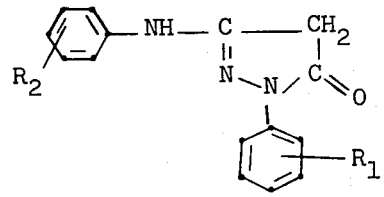

are prepared by reacting a hydrazine of the formula

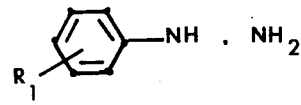

with $\beta,\beta$-dialkoxyacrylic acid ester of the formula

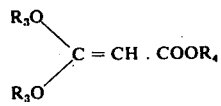

or $\beta,\beta,\beta$-trialkoxy propionic acid ester of the formula

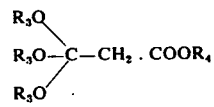

or $\beta$-amino-$\beta$-alkoxy propionic acid ester of the formula

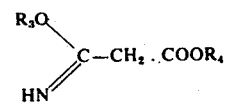

in a methanolic solution with glacial acetic acid as a catalyst to $\beta$-hydrazino-$\beta$-alkoxyacrylic acid ester of the formula

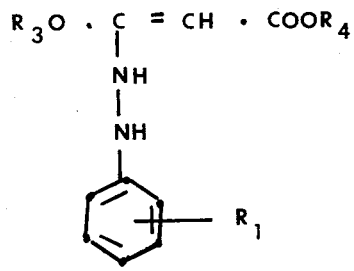

and thereupon reacting this intermediate product with an aniline of the formula

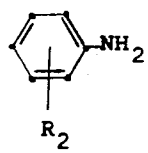

with glacial acid catalyst to the anilinopyrazolone.

In these formulae $R_1$ is H or one or several substituents, customary with respect to phenylpyrazolones, such as alkyl-, alkoxy-, alkylthio-, phenoxy-, halogen-, carboxy-, sulfo acid-, alkyl sulfonic-, carbalkoxy-, carbamido-, sulfofluorido-, cyano-, nitro groups;

$R_2$ is H or one or several substituents such as an alkyl-, alkoxy-, alkylthio-, halogen, alkylsulfonic-, carbamido-, acylamino-, sulfofluorido-, cyano-, nitro group;

$R_3$ and $R_4$ are short-chain alkyl with 1 - 4 carbon atoms, alike or dissimilar.

Detailed Description of the Invention

Quite generally, the following starting materials may for example be used according to the present invention: Hydrazines: Phenylhydrazine, 2,4,6-trichlorophenylhydrazine, 4-methyl-2,6-dichlorophenylhydrazine, 2-chloro-5-methylsulfonylhydrazine, 4-nitrophenylhydrazine. $\beta,\beta$-Dialkoxy acrylic acid ester: These compounds are disclosed in the British Pat. No. 1,129,333 published Oct. 2, 1968 and by Ritter and Weindel, Ber 40 pp. 3358-9 (1907) and Glickman et al J.A.C.S 67 p. 1017 (1945). $\beta,\beta,\beta$-Trialkoxy-propionic acid ester: These compounds may chemically be also designated as semiorthoester of malonic acid. A compound of this type, the $\beta,\beta,\beta$-triethoxypropionate, is disclosed in the literature (McElvain, Schroeder, Am. Soc. 71, 1949, pp. 44, 45) The corresponding trimethoxypropionic acid ethyl ester is very stable in pure form and may particularly well be used according to the invention.

Also disclosed in the literature, e.g. in the British Pat. No. 1,134,329 are $\beta$-alkoxy-$\beta$-iminopropionic esters, the socalled malonic iminoethylesters.

The intermediate products obtained from the hydrazines with the derivatives of acrylic acid or propionic acid in chemical terms are $\beta$-hydrazino-$\beta$-alkoxy acrylic acid esters. They may be stated in two tautomeric forms:

The reaction of the conversion of hydrazine with the acrylic and propionic acid derivative to the hydrazinoalkoxy acrylic acid ester is preferably carried out in a methanol solution; glacial acetic acid serves as catalyst. The hydrazine compounds are usually precipitated from the reaction solution as crystals and may be separated. In some instances, the isolation is not necessary, and after a completed reaction, condensation to pyrazolone may then directly proceed with the aniline, the methanolic solvent optionally being distilled off under reduced pressure.

In the U.S. Pat. No. 2,472,581, such hydrazinoalkoxy acrylic acid esters were prepared already from hydrazines and malonic iminoesters and converted to 3-alkoxypyrazolone. According to the process of the invention, these alkoxy pyrazolones result either not at all or at most in traces. Interesting is also the ascertainment that in the 3-alkoxypyrazolones, an exchange for an aniline residue to 3-anilinopyrazolones is not successful.

Anilines, which may be used according to the invention, are aniline, o-, m- and p-anisidine, o- and p-tetradecyloxyaniline, m- and p-nitraniline, p-aminoacetanilide, anisidinesulfofluoride-(1,2,5).

This invention has a feature that $\beta$-imino-$\beta$-alkoxypropionic ester is reacted with substituted hydrazines. It has been known in the art that the intermediate product $\beta$-hydrazino$\beta$-amino acrylic acid ester is obtained when substituted hydrazines are refluxed with $\beta$-imino-$\beta$-alkoxy propionic acid in ethereal solution in the presence of HCl, see U.S. Pat. No. 2,376,380 of Porter, of Elderfield and particularly of Walter Gregory in U.S. Pat. No. 2,472,581 and of the J.A.C.S., 66 1851 (1944).

According to the present invention, however, $\beta$-hydrazino-$\beta$-alkoxy acrylic ester is obtained in good yields and free of by-products, when the reaction is carried out in methanol as solution and with acetic acid as catalyst even at boiling temperature.

A further novel feature is the conversion of $\beta$-hydrazino-$\beta$-alkoxy acrylic ester to 3-anilino-pyrazolone-(5). The cyclisation is carried out according to the present invention in the presence of an aniline and methanol with acetic acid as catalyst, so that the 3-anilino-pyrazolones are obtained in one step in good yields and substantially free from by-products, such as alkoxy-pyrazolones.

The reaction of the single step method according to the present invention is illustrated by the following equation:

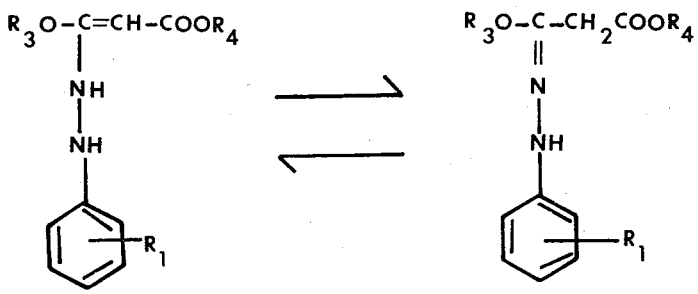

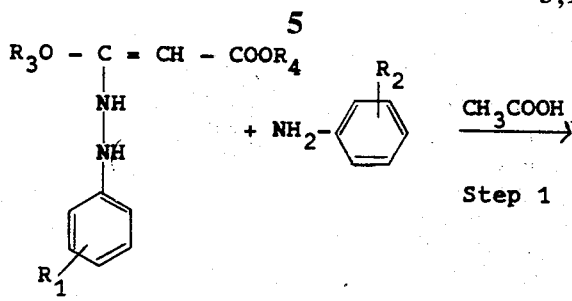

Step 1

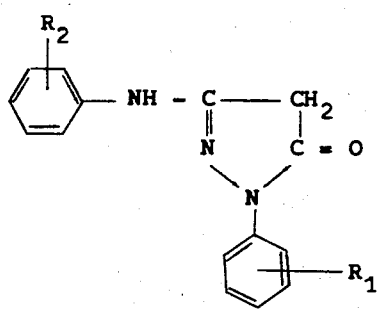

Example 1

1-(2',4',6'-Trichlorophenyl)-3-(4''-acetamidoanilino)-pyrazolone-(5)

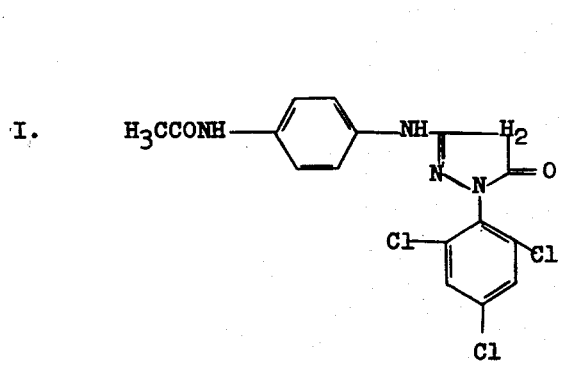

I.

Step 1
3-(2',4',6'-Trichlorophenylhydrazino)-3-methoxyacrylic acid ethyl ester

Into a mixture, which had been brought to a boiling point, consisting of 115 g trimethoxy propionic acid ester, prepared as noted above, 500 ml methanol and 33 ml glacial acetic acid there were added within 20 minutes 105 g 2,4,6-trichlorophenylhydrazine in proportion. Thereupon the mixture was boiled further for 10 minutes, filtered, and the filtrate cooled off. The crystallized product was drawn off, washed with methanol, and dried. Yield: 106 g, i.e. 63% of the theoretical. F. 70°–72°C.

Step 2
Preparation of the pyrazolone of Formula I.

17 g Hydrazinoester of step 1, 8.1 g 4-aminoacetanilide and 10 ml glacial acetic acid were heated for 2 hours on a boiling water bath, the reaction mixture while hot stirred with 50 ml methanol and then cooled. The precipitated product was drawn off and washed with methanol. This represents pyrazolone in a relatively pure form. Yield: 16.3 g, i.e. 80% of the theoretical F. 149°–153°C Example 2

1-(2',4',6'-Trichlorophenyl)-3-(2''-tetradecyloxyanilino)-pyrazolone-(5)

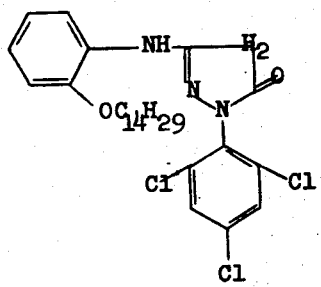

II.

21 g Trichlorophenylhydrazine, 20 g $\beta,\beta$-diethoxyacrylic acid ester and 100 ml methanol were mixed with 10 ml glacial acetic acid. The solution set in during heating. Then it was heated for 10 minutes more on the water bath. It was evaporated under reduced pressure, and to the remaining oil there were added 30.5 g o-tetradecyloxyaniline and 10 ml glacial acetic acid. This mixture was heated for 3 hours on the water bath. The reaction mixture was dissolved hot in 250 ml methanol and allowed to crystallize. Again recrystallized from methanol, obtained were 17 g pyrazolone from the melting point F. 88°–91°C, i.e. 30% of the theoretical.

Example 3

1-(5'-Chloromethylsulfonyl-2'-chlorophenyl)-3-(3''-nitroanilino)-pyrazolone-(5)

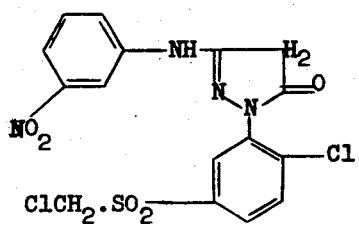

III.

Step 1
3-(5'-Chloromethylsulfonyl-2'-chlorophenylhydrazino)-3-methoxyacrylic acid ethyl ester 12.8 g 5-chloromethylsulfonyl-2-chlorophenylhydrazine, 12 g trimethoxypropionic acid ester, 50 ml methanol and 3.3 ml glacial acetic acid were cooked 15 minutes on a water bath. There resulted a clear solution from which upon cooling the hydrazino compound is crystallized out. This is drawn off, washed with methanol and dried. Yield: 14 g, i.e. 74% of the theoretical. F. 110°–112°C.

Step 2
Pyrazolone Formula III.

9.6 g Hydrazino ester of Step I, 3.5 g m-nitroaniline and 5 ml glacial acetic acid were heated for 3 hours on a water bath, stirred still hot with 20 ml methanol and cooled. The crystal slurry was drawn off and washed with methanol. Yield: 5.5 g, i.e. 50% of the theoretical F. 230°–235°C

What is claimed is:

1. In the process of producing a 1-aryl-3-anilino-pyrazolone-(5) by condensing in two steps a β-substituted acid ester with an aryl hydrazine and an aniline, the improvement according to which the first step of the condensation is effected between the aryl hydrazine and the β-substituted acid ester in methanolic solution with acetic acid as catalyst to form a β-alkoxy-β-aryl-hydrazino-acrylic acid ester wherein the β-substituted acid ester is a β,β,β-trialkoxy-propionic acid ester, a β-imino-β-alkoxypropionic acid ester, or a β,β-dialkoxy-acrylic acid ester, and the second step of the condensation is effected between the aniline and the reaction product of the first step with acetic acid as catalyst.

* * * * *